(12) United States Patent
Aghajanian

(10) Patent No.: US 6,579,378 B1
(45) Date of Patent: Jun. 17, 2003

(54) DE-STAINING COMPOSITION AND APPARATUS

(75) Inventor: Suren Aghajanian, Dublin (IE)

(73) Assignee: Suren Aghajanian, Dublin (IE)

( * ) Notice: Subject to any disclaimer, the term of this patent is extended or adjusted under 35 U.S.C. 154(b) by 0 days.

(21) Appl. No.: 09/959,432

(22) PCT Filed: Apr. 26, 2000

(86) PCT No.: PCT/IE00/00049
§ 371 (c)(1),
(2), (4) Date: Oct. 25, 2001

(87) PCT Pub. No.: WO00/65335
PCT Pub. Date: Nov. 2, 2000

(30) Foreign Application Priority Data

Apr. 26, 1999 (IE) ............................................. S990347

(51) Int. Cl.[7] ................................................. B08B 3/04
(52) U.S. Cl. .................... 134/6; 134/7; 134/38; 134/42; 510/363; 510/475; 252/184; 204/462; 204/463
(58) Field of Search ................ 510/363, 475; 252/184; 204/462, 463; 134/6, 7, 38, 42

(56) References Cited

U.S. PATENT DOCUMENTS

| | | | |
|---|---|---|---|
| 4,021,324 A | 5/1977 | Delony et al. | 204/180 G |
| 4,118,336 A * | 10/1978 | Morishita et al. | 502/62 |
| 4,147,650 A | 4/1979 | Sabatelli et al. | 252/103 |
| 4,357,174 A | 11/1982 | Rushbrook et al. | 134/10 |
| 4,750,506 A | 6/1988 | Olexa | 134/201 |
| 5,564,104 A * | 10/1996 | Pourfarzaneh | 588/20 |
| 6,103,127 A * | 8/2000 | Pourfarzaneh | 210/690 |

FOREIGN PATENT DOCUMENTS

WO  WO 00/653335  * 11/2000

OTHER PUBLICATIONS

Leber et al., Analytical Biochemistry, vol. 249, pp. 24–28, (1997), Article No. AB972170.

* cited by examiner

Primary Examiner—Sharidan Carrillo
(74) Attorney, Agent, or Firm—Birch, Stewart, Kolasch & Birch, LLP

(57) ABSTRACT

The present invention is drawn to a method for de-staining a substrate that is stained with a dye by bringing the substrate into contact with a de-staining composition and absorbing the dye from the substrate with the de-staining composition, wherein the de-staining composition is a charcoal or ion-exchange resin absorbent incorporated in a semi-solid matrix which is a polyacrylamide or agar gel. With the method of the invention a stained substrate may be stained and de-stained in a single step. The present invention is further drawn to an apparatus for performing the method of de-staining the substrate.

10 Claims, 1 Drawing Sheet

DE-STAINING COMPOSITION AND APPARATUS

This application is the national phase under 35 U.S.C. 371 of PCT International Application No. PCT/IE00/00049 which has an International filing date of Apr. 26, 2000, which designated the United States of America and was published in English.

TECHNICAL FIELD

This invention relates to a de-staining composition, in particular a composition for de-staining stained substrates such as electrophoresis gels.

BACKGROUND ART

One of the most widespread techniques in modern molecular biology, biochemistry, clinical analysis etc. is electrophoresis as performed on polyacrylamide or other gels. In this procedure a mixture of substances, typically proteins or peptides, in a biological sample is separated by virtue of the differential mobility of the individual components in an electrical field. For this method to be useful it is necessary to reveal the usually colourless separated bands of material.

Typically in such gel-electrophoresis procedures, the development of the bands corresponding to the individual proteins, peptides or other biological compounds under investigation requires a step in which these compounds are stained with dyes, typically lasting 30–60 min. This is generally then followed by a separate and lengthy de-staining step for example in a methanol-acetic acid mixture to remove excess dyes from the gel thus clearing the background so that the stained bands may be seen. Usually the de-staining step takes a much longer time than the staining step.

Used de-staining solutions are typically recycled by passing through a column of activated charcoal or ion exchange resin, which binds the excess staining dyes. More often, in research laboratories, simple funnels, filled with activated charcoal, are used instead of columns. This requires use of a fume hood to remove the harmful vapours of the solvent, typically methanol and acetic acid.

U.S. Pat. No. 4,357,174 describes a de-staining apparatus where a stain absorbing material (granulated charcoal) is located in a housing with apertures and retained therein by a porous material disposed around the internal walls of the housing. However, the efficiency of this apparatus is limited by the surface area of the apertures restricting the amount of de-staining fluid allowed to flow into and out of the housing.

Other proposals have been made for simplifying the various de-staining techniques such as diffusion, in-flow filtration and use of electrical fields. However, these proposals involve either high cost apparatus requiring highly qualified personnel and sophisticated techniques for production and/or suffer from relatively low efficiency such as in U.S. Pat. No. 4,357,174 as described above.

It is an object of the present invention to address these problems by providing inter alia a cheap, efficient and easy to use de-staining composition.

DISCLOSURE OF INVENTION

The invention therefore provides a de-staining composition for de-staining a stained substrate, which composition comprises an absorbent for the stain incorporated in a semi-solid matrix.

Advantages of the compositions according to the invention reside inter alia in their adaptability to different uses, ease of handling and convenience.

The semi-solid matrix can be made from any material which will permit incorporation of the absorbent and remain semi-solid once the absorbent is incorporated and in use.

Preferably the semi-solid matrix is a gel.

An especially preferred gel is a polyacrylamide or agar gel.

When an agar gel is employed it is preferred that the agar gel is an agarose gel.

Suitable absorbents for the stain include charcoals (activated or otherwise) or ion exchange resins such as styrene-divinyl benzene copolymers having sulfonic acid or quaternary amine groups.

Preferred absorbents for the stain are activated charcoal or a mixture of ion exchange resins.

The absorbent material will typically be incorporated into the semi-solid matrix prior to or during formation of the latter by mixing. Thus, by way of example, in the case of an agar gel the absorbent is mixed into a heated suspension or solution of the agar which is then allowed to set in appropriately sized moulds. In the case of polyacrylamide gels the absorbent may be mixed into the acrylamide prior to polymerisation.

The concentration of the gel itself and of the absorbent incorporated therein will be chosen in accordance with the particular use for which the composition is intended and will be within the competency of the skilled person.

For example, in the case of gels, the concentration will preferably be in the range of 0.5 to 10% w/v, especially 1 to 5% w/v.

In these gels, the concentration of absorbent will preferably be in the range of 0.5 to 10% w/v especially 2 to 5% w/v.

The size and shape of the semi-solid matrix once formed will be chosen in accordance with the type of substrates it is desired to de-stain, the apparatus in which de-staining is to take place and the capacity of the composition in terms of its ability to absorb stain.

Preferably, the semi-solid matrix with the absorbent will be capable of being used a number of times before discarding or regenerating as desired.

According to a further aspect of the invention there is provided a method for de-staining a stained substrate, which method comprises bringing the substrate to be de-stained into contact with a de-staining composition as hereinbefore defined under conditions which will bring about release of the stain from the stained substrate.

Preferably, the de-staining composition and the substrate to be de-stained are brought into contact with a de-staining solution comprising a solvent or mixture of solvents capable of bringing about release of the stain from the stained substrate.

This method is of particular value when the substrate to be de-stained is a developed electrophoresis gel.

The solvent or mixture of solvents employed as the de-staining solution in the method according to the invention will be chosen in accordance with the nature of the stain it is desired to extract and absorb and the nature of the substrate which is to be de-stained. This choice will be within the capability of the skilled person in this field.

Typically the de-staining solution is or comprises an organic solvent.

De-staining solutions are preferred wherein the solvent is or comprises an alcohol. A preferred such solvent is an aqueous alcohol. Examples of alcohols include methanol, ethanol and butanol.

Other solvents may optionally be added to the de-staining solution.

Thus, optionally, the de-staining solution additionally comprises an organic acid. An example of such an organic acid is acetic acid.

A particularly preferred de-staining solution comprises aqueous methanol and acetic acid.

In carrying out the method in accordance with the invention the substrate to be de-stained and the composition according to the invention are brought together in such a way as to allow de-staining to take place. This can be achieved for example by placing the substrate to be de-stained and the composition according to the invention together with a de-staining solution capable of bringing about release of the stain in question in a suitable receptacle.

In a further aspect of the invention there is provided a method for carrying out staining and de-staining in a single operation. Thus, by using a staining solution of suitable composition, the entity to be stained will take up sufficient stain to achieve the requisite staining while simultaneously the de-staining composition will remove any excess stain so that the staining and de-staining steps need not be separated.

Thus, in one embodiment of the invention the de-staining composition is effective to remove any excess stain from a substrate, such that staining and de-staining can be carried out in a single operation.

Preferably, the de-staining composition is pre-equilibrated with the de-staining solution.

Further, preferably, the staining compound is in the form of a solution of said de-staining solution at a concentration in the range 0.01–0.1% w/v.

In this embodiment of the invention, the concentration of the absorbent for the stain entrapped in the semi-solid matrix has to be sufficient to capture all excess stain from the staining solution without bleaching the bands of the entity to be stained. As hereinafter demonstrated, we have established the necessary optimal conditions to achieve satisfactory results.

This aspect of the invention can be considered as a staining method which obviates the need for a separate de-staining step because the absorbent for the stain incorporated in the semi-solid matrix allows for the removal of excess stain in a single operation.

This aspect of the invention offers convenience to the scientist who, for example, runs an electrophoresis gel at the end of a day, is unable to wait for the gel to stain but nevertheless wishes to see the results first thing the next day.

Experimentally, it has been shown that if one uses solutions with dye concentrations of 0.01–0.1% w/v and methanol (10–30% v/v) and acetic acid (5–15% v/v), it is possible to get a clear background on a gel with sharp and well-stained protein bands over approximately 3–20 h depending on the composition of the solutions used.

References hereinafter to de-staining should also be read as embracing simultaneous staining and de-staining in accordance with the invention.

The stain as used herein is typically a dye, more especially a dye for proteins selected from Coomassie, Eosin, Procion, Cibacron, Fast and other dyes.

Examples of Coomassie dyes are:
Coomassie® Brilliant Blue R-250 (Brilliant Blue R);
Coomassie® Brilliant Blue G-250 (Brilliant Blue G);
Coomassie® Brilliant Cresyl Blue (Brilliant Blue C);
Coomassie® Brilliant Green; and
Coomassie® Violet R-200.

Examples of Eosin dyes are:
Eosin Yellowish (Eosin Y);
Eosin Scarlet, and others.

Examples of Procion® dyes are Procion® Blue MX-R and others.

Examples of Cibacron® dyes are Cibacron[\R] Blue F3G-A and others.

Examples of Fast dyes are:
Fast Green FCF (Food Green 3);
Fast Blue B Salt and others Examples of other dyes include:
Naphthol Blue Black (Amino Black 10B);
Alcian Blue 8GX (Ingrain Blue 1);
Drimarene Brilliant Blue K-BL and others.

Probably the most commonly used dye is Coomassie® (Brilliant Blue R-250 (Brilliant Blue R) and the invention will hereinafter be illustrated with respect to this dye.

According to a further aspect the invention there is provided an apparatus for de-staining a stained substrate, which apparatus comprises a receptacle containing a de-staining composition as hereinbefore defined and which is capable of receiving and containing both the substrate to be de-stained and a de-staining solution comprising a solvent or mixture of solvents capable of bringing about release of the stain from the stained substrate.

Preferably, the semi-solid matrix forms a layer covering the base of the inside of the receptacle.

Alternatively, the semi-solid matrix is in the form of a block which will float in the de-staining solution when added to the receptacle.

The size and shape of the receptacle will be chosen in accordance with the substrate to be de-stained. For example when the substrate to be de-stained is an electrophoresis gel the receptacle will be in the form of a dish or tray.

The receptacle is made from a material which is inert to the de-staining solution. Suitable materials include glass and plastics materials such as methylmethacrylate.

Preferably, the receptacle is made from a transparent material. This allows a user to follow the de-staining process without having to open the apparatus.

Optionally, the receptacle bears a lid. This helps to reduce evaporation of the de-staining solution.

Preferably, the lid is made of a transparent material.

When the apparatus is of the base-covered type, all or part of the bottom of the receptacle will be provided with a white background to make detection of the gel background during the de-staining process easier.

The contents of the receptacle when in use, namely de-staining solution, substrate and de-staining composition can be agitated in conventional manner by direct stirring or by shaking and/or rocking on a conventional apparatus of the type used in electrophoresis.

In one embodiment the de-staining composition is effective to remove any excess stain from a substrate, such that staining and de-staining can be carried out in a single operation.

Preferably, the staining composition is pre-equilibrated with the de-staining solution.

Further, preferably, the staining compound is in the form of a solution of said de-staining solution at a concentration in the range 0.01–0.1% w/v.

The invention will be further illustrated by the following description of embodiments thereof, given by way of example only with reference to the accompanying drawings.

BRIEF DESCRIPTION OF DRAWINGS

In FIG. 1 there is indicated, generally at 10, a de-staining apparatus which comprises a receptacle 11, made of a transparent material such as glass or plastics material, bearing a lid 12 of the same or different material which covers the receptacle 11 and rests on the upper rim 13 thereof.

Figure 1:
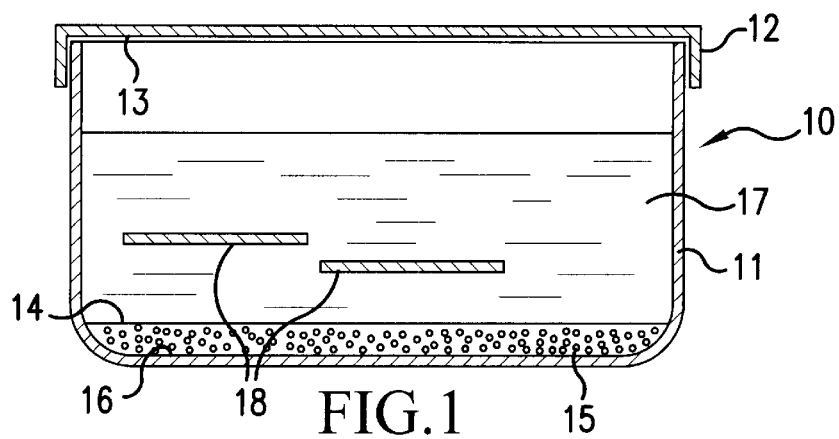
FIG. 1 is a cross section of a de-staining apparatus according to the invention.

The receptacle 11 contains a semi-solid matrix 14 which is made of a gel such as agarose gel and contains a stain absorbent 15 such as finely divided, activated charcoal. The semi-solid matrix 14 covers base 16 of the receptacle 11.

The receptacle 11 further contains a de-staining solution 17 in which the substrates to be de-stained 18 are immersed.

Figure 2:
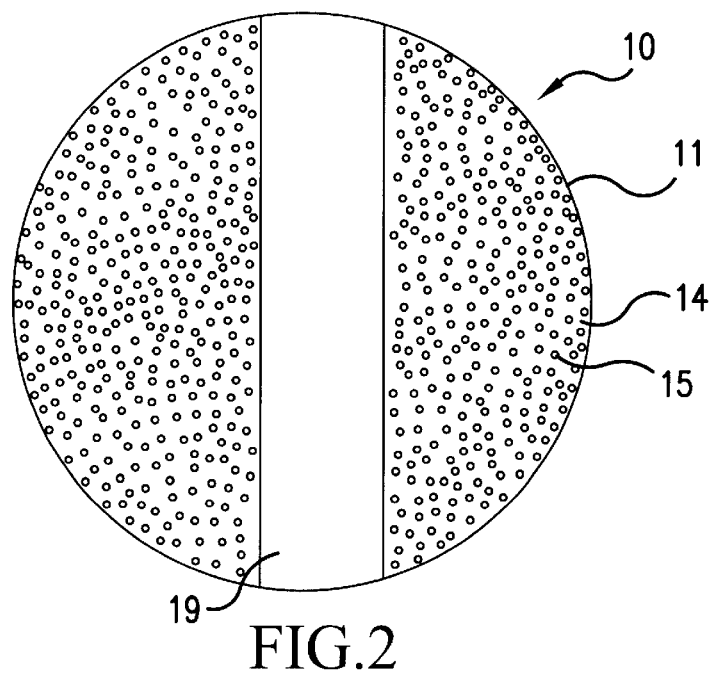
FIG. 2 is a plan view from beneath of the apparatus shown in FIG. 1.

FIG. 2 shows the receptacle 11 from beneath through which the semi-solid matrix 14 and the stain absorbent 15 can be seen. The receptacle 11 has a strip 19 of white or otherwise pale material across the bottom.

To use the apparatus 10, the receptacle 11 with the semi-solid matrix 14 incorporating the absorbent 15 across its base 16 contains the gels to be de-stained 18 and the de-staining solution 1 7. The apparatus 10 is placed on a conventional shaker (not shown) and agitated until the gels have been de-stained to the desired extent. The de-staining process can be tracked by viewing the gels 18 against the white background 19 through the lid 12.

Depending on the capacity of the stain absorbent 15 the apparatus can be used to de-stain further gels by immersing them in the solvent which itself can be topped up as needed.

Once the de-staining capacity of the compostion is exhausted the apparatus may simply be discarded or the receptacle recycled by removing the exhausted de-staining composition, cleaning the receptacle and recharging it with fresh de-staining composition.

Figure 3:
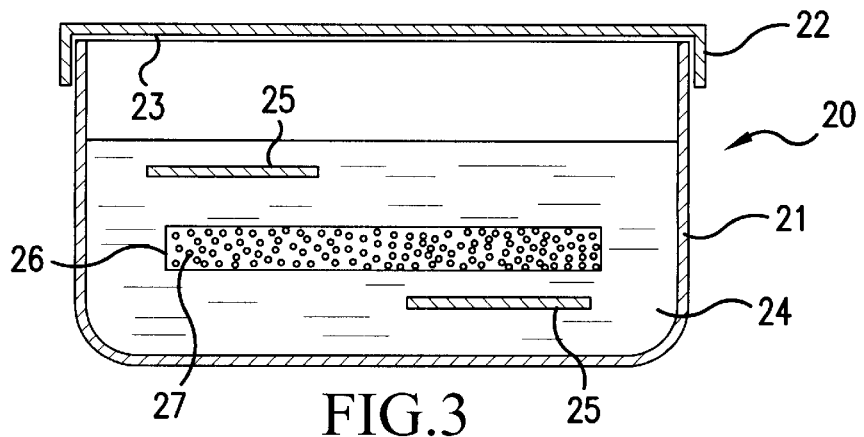
FIG. 3 is a cross section of an alternative embodiment of a de-staining apparatus according to the invention.

In FIG. 3 the apparatus shown generally at 20 comprises a receptacle 21, made of a transparent material such as glass or plastics material, bearing a lid 22 of the same or different material which covers the receptacle 21 and rests on the upper rim 23 thereof.

The receptacle 21 further contains a de-staining solvent 24 in which the substrates 25 to be de-stained are immersed. Also immersed in the solvent 24 is a block of semi-solid matrix 26 incorporating a stain absorbent 27.

The apparatus may be used in substantially the same manner as described above for FIGS. 1 and 2.

The following Examples illustrate the manner of carrying out the invention without in any way restricting the scope thereof.

MODES FOR CARRYING OUT THE INVENTION

EXAMPLE 1

Absorption of Protein Staining Dye

Four different concentrations of agar gels (0.5, 1, 1.5 and 2% w/v) containing four different concentrations of activated charcoal (0.5, 1, 2 and 5% w/v) were made from 4% stock solution of agar and 10% stock suspension of activated charcoal in water.

De-staining trays with a bottom surface of ca. 60 cm were covered with 20 ml of agar gel (thickness ca. 3 mm). 30 ml of de-staining solution (methanol/acetic acid/water 3:1:6 v/v) containing staining dye [Coomassie® Brilliant Blue R-250; Coomassie is a Trade Mark of Imperial Chemical Industries] was applied (with optical density at 600 nm equal 1). The time course of absorption of the dye by the activated charcoal was determined by following the change in optical density of the solution at 600 nm.

From the results shown in Table 1 it is clear that practically complete removal of the staining dye from the solution was achieved in 2 hrs or less for the concentrations of activated charcoal in the range of 2–5% and for agar gels with concentrations higher than 0.5%.

TABLE 1

Time in hours for absorption of staining dye.

| % charcoal → <br> % agar gel ↓ | 0.5% | 1.0% | 2.0% | 5.0% |
|---|---|---|---|---|
| 0.5% | 8 | 6 | 3.5 | —* |
| 1.0% | 5 | 3 | 2 | 1.5 |
| 1.5% | 3 | 2 | 1.5 | 1 |
| 2.0% | 2.5 | 2 | 1.5 | 1 |

*Poor polymerisation of agar at low concentration in the presence of high concentrations of charcoal.

EXAMPLE 2

De-staining of Polyacrylamide Electrophoresis Gels

The gel and activated charcoal concentrations are shown in Table 2. The de-staining solution was the same as that used in Example 1. De-staining trays with a bottom surface of ca. 150 cm were covered to a thickness of ca. 2 mm with agar gel and 50 ml of stock de-staining solution (the same as that used in Example 1) or the same de-staining solution at two-fold dilution were added.

The substrates to be de-stained were 12% mini polyacrylamide electrophoresis gels (8×10 cm) with 0.75 mm thickness which had been stained for 1 hr with Coomassie® Brilliant Blue R-250.

Eight such polyacrylamide gels were placed in the de-staining solution, one in each tray, and the destaining process monitored visually every 30 minutes.

The results are shown in Table 2. At almost all gel and charcoal concentrations destaining of the background of the electrophoresis gels was complete in approximately 2 hrs in stock solution and 3.5–4 hrs using the two-fold diluted solution.

The same trays were employed in four subsequent de-staining cycles using newly stained-electrophoresis gels. Only moderate loss of de-staining power was seen even on the fourth cycle (see Table 2).

TABLE 2

Time in hours for de-staining of polyacrylamide electrophoresis gels.

| Composition | De-staining solution | I cycle of de-staining | II cycle of de-staining | III cycle of de-staining | IV cycle of de-staining |
|---|---|---|---|---|---|
| 1% agar/ 2% charcoal | Stock 2-fold diluted | 2–2.5 3.5–4 | 2–2.5 4–4.5 | 2–2.5 4–4.5 | 2.5–3 5–5.5 |
| 1% agar/ 5% charcoal | Stock 2-fold diluted | 2 3.5–4 | 2 3.5–4 | 2–2.5 4–4.5 | 2–2.5 4–4.5 |
| 2% agar/ 2% charcoal | Stock 2-fold diluted | 2 3.5–4 | 2 3.5–4 | 2–2.5 4–4.5 | 2–2.5 4–4.5 |
| 2% agar/ 5% charcoal | Stock 2-fold diluted | 2 3.5–4 | 2 3.5–4 | 2 3.5–4 | 2.5 4–4.5 |

EXAMPLE 3

Combination of Staining and De-staining Processes in One Step

Trays with approximately 150 cm² bottom surface covered with 2 mm of two different concentrations of agar gels (1 and 2% w/v) and activated charcoal (2% w/v) were used. These trays were previously equilibrated with solutions of different mixing ratios of methanol/acetic acid/water (30/10/60; 20/10/70 or 15/7.5/77.5% v/v). The excess of liquid from the trays was removed just before use.

12% mini polyacrylamide electrophoresis gels (8×10 m) and of 0.75 mm thickness were tested. After electrophoresis these polyacrylamide gels were placed in the pre-equilibrated trays and 50 ml combined staining and de-staining solutions with different concentrations of the dye Coomassie ® Blue R-250 in a solution with different ratios of methanol/acetic acid/water were added as shown in Table 3. The combined process of staining and de-staining of the gels (protein bands and background of the gel) was monitored visually every 30 min. The results are shown in Table 3. In practice we have shown that if one uses combined solutions with dye concentrations of 0.01–0.1% and methanol (MET) (10–30%) and acetic acid (AA) (5–15%) one can obtain a clear background on the gel with well-stained protein bands over an approximately 3–20 h time period depending on the composition of the solutions used. The results shown in Table 3 fall within these ranges.

It will be appreciated that the concentration of dye has to be high enough to stain the protein bands properly. However, because of the limited solubility of the dye in water, the concentration of methanol/acetic acid has to be high enough also to prevent precipitation of the dye. An increase of methanol/acetic acid concentration beyond the indicated range will result in a negative effect—bleaching of the dye from protein bands. Therefore the optimum condition has to be found. Specifically in this Example we found that when we used a combined staining and de-staining solution with 0.025% Coomassie® Blue R-250 in 15% methanol and 7.5–10% acetic acid we obtained a clear background on the 0.75 mm electrophoresis gels with sharp and well-stained protein bands over the period of time 10–15 h.

TABLE 3

Content of combined staining and de-staining solutions and time required for processing of polyacrylamide electrophoresis gels

| Bottom gels Agar/Charcoal | Combined solution of dye in methanol/acetic acid (%) | Time required | Background | Protein bands |
|---|---|---|---|---|
| 1/2 | 0.05% dye in 30% Met/10% AA | 5–10 | ** | *** |
| 1/2 | 0.05% dye in 20% Met/10% AA | 10–15 | ** | *** |
| 1/2 | 0.025% dye in 30% Met/10% AA | 5–10 | *** | ** |
| 1/2 | 0.025% dye in 20% Met/10% AA | 5–10 | *** | ** |
| 1/2 | 0.025% dye in 15% Met/7.5% AA | 10–15 | *** | *** |
| 1/2 | 0.01% dye in 20% Met/10% AA | 3–15 | *** | ** |
| 1/2 | 0.01% dye in 15% Met/7.5% AA | 5–10 | *** | * |
| 2/2 | 0.05% dye in 30% Met/10% AA | 5–10 | ** | *** |
| 2/2 | 0.05% dye in 20% Met/10% AA | 10–15 | ** | *** |
| 2/2 | 0.025% dye in 30% Met/10% AA | 5–10 | *** | ** |
| 2/2 | 0.025% dye in 20% Met/10% AA | 5–10 | ** | *** |
| 2/2 | 0.025% dye in 15% Met/7.5% AA | 10–15 | *** | *** |
| 2/2 | 0.01% dye in 20% Met/10% AA | 3–5 | *** | ** |
| 2/2 | 0.01% dye in 15% Met/7.5% AA | 5–10 | *** | * |

In Table 3 qualities of background and protein bands are as follows
For background:
* - Blue background
** - Light bluish background
*** - Clear background
For protein bands:
* - Pale or bleached bands
** - Bands with moderate intensity
*** - Sharp and well-stained bands

What is claimed is:

1. A method for de-staining a substrate that is stained with a dye, which method comprises bringing the substrate into contact with a de-staining composition and absorbing said dye from said substrate with said de-staining composition, wherein said de-staining composition is a charcoal or ion-exchange resin absorbent incorporated in a semi-solid matrix which is a polyacrylamide or agar gel.

2. A method according to claim 1, further comprising bringing the de-staining composition and the substrate in contact with a de-staining solution comprising a solvent or mixture of solvents that release the dye from the stained substrate.

3. A method according to claim 1 or 2, wherein the de-staining solution comprises an organic solvent.

4. A method according to claim 2, wherein the de-staining solution comprises aqueous methanol and acetic acid.

5. A method of staining a substrate with a dye and de-staining the substrate with a de-staining composition in a single step which comprises bringing the substrate into contact with a) a staining solution containing said dye, and b) a de-staining composition, wherein said de-staining composition is a charcoal or ion-exchange resin absorbent incorporated in a semi-solid matrix which is a polyacrylamide or agar gel and wherein said substrate is stained by said staining solution and de-stained by said de-staining composition in a single step.

6. A method according to claim 5, wherein the de-staining composition is pre-equilibrated, prior to contact with the substrate, with a de-staining solution comprising a solvent or mixture of solvents that releases the dye from the stained substrate.

7. A method according to claim 5 or 6, wherein the staining solution comprises a solution of solvents that release the dye from the substrate and a staining compound at a concentration in the range 0.01–0.1% w/v.

8. An apparatus for de-staining a substrate that is stained with a dye, which apparatus comprises a receptacle containing a de-staining composition that absorbs said dye from said substrate; and which receives and contains both the substrate and a de-staining solution comprising a solvent or mixture of solvents that releases the dye from the stained substrate, wherein said de-staining composition is a charcoal or ion-exchange resin absorbent incorporated in a semi-solid matrix which is a polyacrylamide or agar gel.

9. An apparatus according to claim 8, further comprising a staining solution, wherein the de-staining composition removes excess dye from the substrate, such that staining and de-staining can be carried out in a single operation.

10. An apparatus according to claim 8 or 9, wherein the de-staining composition is pre-equilibrated, prior to contact with the substrate, with a de-staining solution comprising a solvent or mixture of solvents that releases the dye from the stained substrate.

* * * * *